United States Patent [19]
Stemerick

[11] Patent Number: 5,665,715
[45] Date of Patent: Sep. 9, 1997

[54] FARNESYL:PROTEIN TRANSFERASE INHIBITORS AS ANTICANCER AGENTS

[75] Inventor: David M. Stemerick, Fairfield, Ohio

[73] Assignee: Merrell Pharmaceuticals Inc., Cincinnati, Ohio

[21] Appl. No.: 508,958

[22] Filed: Jul. 28, 1995

Related U.S. Application Data

[62] Division of Ser. No. 148,188, Nov. 8, 1993, Pat. No. 5,463,181, which is a continuation of Ser. No. 21,411, Feb. 23, 1993, abandoned.

[51] Int. Cl.$^6$ .................................................. A61K 31/66
[52] U.S. Cl. ........................................ 514/125; 514/129
[58] Field of Search ................................ 514/125, 129

[56] References Cited

U.S. PATENT DOCUMENTS

| | | |
|---|---|---|
| 4,541,858 | 9/1985 | Pfister et al. |
| 4,924,024 | 5/1990 | Biller et al. |
| 5,177,239 | 1/1993 | Singh et al. |

FOREIGN PATENT DOCUMENTS

| | | |
|---|---|---|
| 0534546 | 3/1993 | European Pat. Off. |
| 0 168 709 | 1/1996 | European Pat. Off. |
| 57-142993 | 9/1982 | Japan |

OTHER PUBLICATIONS

Schafer, et al., Science 245:379–385 (1989).
Bos, Cancer Research, 49:4682–4689 (1989).
Pompliano, et al., Biochemistry 31:3800–3807 (1992).
Maltese, FASEB Journal 4:3319–3328 (1990).
Casey, et al., Proc. Natl. Acad. Sci. USA 86:8323–8327 (1989).
Goldstein, et al., J of Biological Chemistry 266(24):15575–15578 (1991).
Cox, et al., Molecular and Cellular Biology 12(6):2606–2615 (1992).
Biller, et al., Tetrahedron 46(19):6645–6658 (1990).
Burton, et al., Chem. Lett. 5:755–58 (1982).
Obayashi, et al., Tetrahedron Letters 23(22):2323–2326 (1982).
Pfister, et al., Chem. Abstracts 102(13):113737p pg. 738, Apr. 1, 1985.
Halazy, et al., J. Chem. Soc. Chemical Communications 10:733–743–745 (1982).
Moskva, et al., Chem. Abstracts 107(23)::217736g, 1987.

*Primary Examiner*—Johann Richter
*Assistant Examiner*—Michael G. Ambrose
*Attorney, Agent, or Firm*—David M. Stemerick; Nelsen L. Lentz

[57] ABSTRACT

The present invention relates to certain inhibitors of farnesyl:protein transferase which are useful as antineoplastic agents.

2 Claims, No Drawings

FARNESYL:PROTEIN TRANSFERASE INHIBITORS AS ANTICANCER AGENTS

This is a division of application Ser. No. 08/148,188, filed Nov. 8, 1993, now U.S. Pat. No. 5,467,182, which is a continuation of application Ser. No. 08/021,411 filed Feb. 23, 1993, now abandoned.

BACKGROUND OF THE INVENTION

The ras family of oncogenes and proto-oncogenes encode certain proteins which are implicated in the control of eukaryotic cell proliferation. These genes, through the normal transcription and translational processes, provide proteins called ras proteins which can interact with effector molecules to control cell division.

Ras proteins are initially produced in the cell in an inactive state and must undergo various post-translational modifications in order to become activated. As part of the activation process, the ras proteins undergo farnesylation at a cysteine residue located near the C-terminus. This farnesylation facilitates the association of the ras protein with the inner surface of the plasma membrane. Membrane association is critical for the oncogenic transformation caused by activated ras proteins. See Schafer et al., Science 245, 379 (1989).

The farnesylation of ras proteins is catalyzed by the enzyme ras farnesyl:protein transferase, also known as FPTase. Through this enzymatic reaction, the farnesyl moiety of the cholesterol biosynthetic intermediate, farnesyl diphosphate, is linked through a thioether bond to a cysteine residue located near the C-terminus of the ras protein.

Activated ras proteins are found in a variety of human cancers including colon and pancreatic carcinomas. Interference of membrane localization by ras proteins by inhibition of the FPTase-mediated farnesylation of inactive ras proteins, will inhibit cell proliferation caused by activated ras proteins and will thus provide an anticancer effect.

The present invention provides compounds which are inhibitors of ras FPTase and as such are useful as anticancer agents.

SUMMARY OF THE INVENTION

The present invention provides compounds having the following general formula:

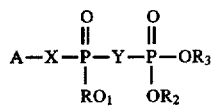

Formula I wherein X is $CH_2$, $CCl_2$ or $CF_2$, $R_1$ and $R_2$ are each independently H; $C_1$-$C_4$ alkyl; $(CH_2)_n$-Z, wherein n is the integer 0,1,2,3 or 4 and Z is phenyl or naphthyl, unsubstituted or substituted with from 1 to 3 substituents selected from the group consisting of $C_1$-$C_4$ alkyl, $C_1$-$C_4$ alkoxy, halogen, $CF_3$, $OCF_3$, OH, CN, $NO_2$ and $NH_2$; or a pharmaceutically acceptable cation, and A is a radical selected from the group consisting of

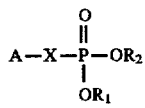

wherein $R_3$ is $C_1$-$C_{19}$ alkyl which can be saturated or unsaturated having from 1 to 9 double bonds.

The present invention also provides compounds having the following general formula:

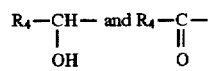

Formula II wherein X is $CH_2$, $CCl_2$ or $CF_2$,

Y is $CH_2$ or $CF_2$, $R_1$, $R_2$ and $R_3$ are each independently H; $C_1$-$C_4$ alkyl; $(CH_2)_n$-Z, wherein n is the integer 0,1,2,3 or 4 and Z is phenyl or naphthyl, unsubstituted or substituted with from 1 to 3 substituents selected from the group consisting of $C_1$-$C_4$ alkyl, $C_1$-$C_4$ alkoxy, halogen, $CF_3$, $OCF_3$, OH, CN, $NO_2$ and $NH_2$; or a pharmaceutically acceptable cation, and A is a radical selected from the group consisting of

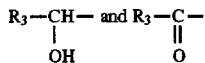

wherein $R_4$ is $C_1$-$C_{19}$ alkyl which can be saturated or unsaturated having from 1 to 9 double bonds.

Another embodiment of the present invention is a method of treating a patient afflicted with a neoplastic disease state or of controlling the growth of a neoplasm in a patient afflicted with a neoplastic disease state comprising administration of a therapeutically effective antineoplastic amount of a compound of Formula I or II.

DETAILED DESCRIPTION OF THE INVENTION

As used herein the term "$C_1$-$C_4$ alkyl" refers to a saturated straight or branched chain hydrocarbon radical of one to four carbon atoms. Included within the scope of this term are methyl, ethyl, n-propyl, isopropyl, n-butyl, isobutyl, and the like. The term "$C_1$-$C_4$ alkoxy" refers to an alkyloxy radical made up of an oxygen radical bearing an saturated straight or branched chain hydrocarbon radical of one to four carbon atoms included within the scope of this term are methoxy, ethoxy, propyloxy, isopropyloxy, n-butyloxy, isobutyloxy, sec-butyloxy, t-butyloxy and the like. The term "$C_1$-$C_{19}$ alkyl which can be saturated or unsaturated having from 1 to 9 double bonds" refers to a branched or straight chain hydrocarbon radical of from one to nineteen carbon atoms. Included specifically within the scope of this term are methyl, ethyl, n-propyl, isopropyl, n-butyl, isobutyl, pentyl, hexyl, heptyl, octyl, nonyl, decyl, undecyl, dodecyl, tridecyl, tetradecyl, pentadecyl, hexadecyl, heptadecyl, octadecyl, nonadecyl, farnesyl, geranyl, neryl, 3-methyl-2-butenyl and the like. The term "halogen" refers to a chlorine, bromine or iodine atom. The term "Pg" refers to a protecting group. The term "pharmaceutically acceptable cation" refers to those cations that are not substantially toxic at the dosage administered to achieve the desired effect and do not independently possess significant pharmacological activity. The salts included within the scope of this term are those of alkali metals, as for example, sodium and potassium; alkaline earth metals, such as calcium and magnesium; light metals of Group IIIA including aluminum; and organic primary, secondary and tertiary amines, as for example, triethylamine, dibenzylamine, N,N'-dibenzylethylenediamine, diisopropyl ethylamine and the like. Sodium salts are preferred.

The compounds of of Formula I can be prepared as described in Scheme I. All the substituents, unless otherwise indicated, are previously defined. The reagents and starting materials are readily available to one of ordinary skill in the art.

Scheme I

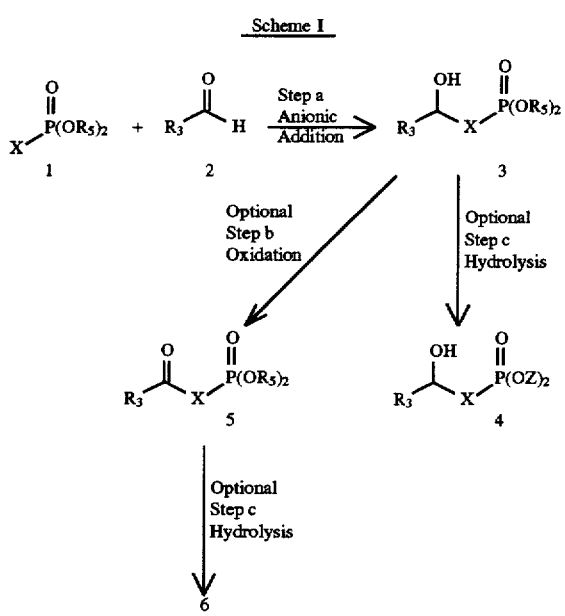

$R_5 = R_1$ and $R_2$ with the proviso that $R_5$ is not hydrogen or a pharmaceutically acceptable cation.

$Z =$ hydrogen or a pharmaceutically acceptable cation

In Scheme I, step a, the aldehyde defined by structure (2) is treated with the anion of the phosphonate defined by structure (1) to provide the alcohol defined by structure (3). For example, an equivalent of the appropriately substituted phosphonate (1), such as dimethyl difluoromethylphosphonate dissolved in a suitable organic solvent, such as tetrahydrofuran, is added dropwise to a stirring solution of lithium diisopropylamide at approximately −78° C. The mixture is stirred for 2 minutes to 2 hours. An appropriately substituted aldehyde (2), such as farnesal [prepared by a Swern Oxidation of trans, transfarnesol following the procedure of Biller, S. A. and Forster, C., Tetrahedron 1990, 46(19), 6645] dissolved in a suitable organic solvent, such as tetrahydrofuran, is slowly added to the anion of (1) maintaining the reaction temperature below −72° C. After approximately 2 hours the reaction is poured into a suitable aqueous acid, such as 0.1N hydrochloric acid, and extracted with a suitable organic solvent, such as diethyl ether. The organic phase is dried over a suitable drying agent, such as anhydrous magnesium sulfate, filtered and concentrated under vacuum. The residue is then purified by techniques well known in the art. For example, the residue can be purified by flash chromatography using a suitable organic eluent, such as 40% ethyl acetate/hexane to provide dimethyl 1,1-difluoro-2-hydroxy-4,8,12-trimethyl-3,7,11-tridecatrienylphosphonate.

In Scheme I, step b, the alcohol (3) is oxidized to the ketone described by structure (5). For example, an equivalent of trifluoroacetic acid anhydride is added dropwise to 2 equivalents of dimethylsulfoxide in a suitable organic solvent, such as dichloromethane at approximately −60° C. After addition is complete, the reaction is stirred for approximately 2 minutes. An equivalent of an appropriately substituted alcohol (3), such as dimethyl 1,1-difluoro-2-hydroxy-4,8,12-trimethyl-3,7,11-tridecatrienylphosphonate dissolved in a suitable organic solvent, such as dichloromethane, is added to the reaction dropwise. After addition is complete, the reaction is stirred for approximately 45 minutes. The reaction is then cooled to −78° C. and an excess of triethylamine is added dropwise. The reaction is then allowed to warm to ambient temperature and stirred for approximately 45 minutes. The reaction mixture is then poured into water and extracted with a suitable organic solvent, such as diethyl ether. The organic phase is dried over a suitable drying agent, such as anhydrous magnesium sulfate, filtered and concentrated under vacuum. The residue is then purified by techniques well known in the art. For example, the residue can be purified by flash chromatography using a suitable organic eluent, such as 20% ethyl acetate/hexane, to provide dimethyl 1,1-difluoro-2-oxo-4,8,12-trimethyl-3,7,11-tridecatrienylphosphonate.

In Scheme I, step c, the alcohol defined by structure (3) is hydrolyzed to the diacid or salt of the diacid defined by structure (4). For example, an appropriately substituted alcohol (3), such as dimethyl 1,1-difluoro-2-hydroxy-4,8,12-trimethyl-3,7,11-tridecatrienylphosphonate, is combined with approximately 2 equivalents of collidine in a suitable organic solvent, such as dichloromethane, and cooled to approximately 0° C. Approximately 4 equivalents of a suitable trialkylsilyl halide, such as trimethylsilyl iodide, is added dropwise to the above solution. After stirring for about 2 hours, the reaction is diluted with a suitable organic solvent, such as diethyl ether, and rinsed with a suitable aqueous acid, such as 1N hydrochloric acid. The organic phase is then dried over a suitable drying agent, such as anhydrous sodium sulfate, filtered and concentrated under vacuum to provide the crude diacid. This is treated with a suitable base, such as 0.1N sodium hydroxide, and then lyophitlized to remove the water. The product is then purified by techniques well known in the art. For example, the product can be purified by chromatography on a suitable stationary phase, such as CHP20P (a divinylbenzene/styrene copolymer) with an suitable eluent, such as a gradient from water to methanol, to provide the disodium salt of 1,1-difluoro-2-hydroxy-4,8,12-trimethyl-3,7,11-tridecatrienylphosphonic acid.

In Scheme I, step c, the ketone defined by structure (5) is hydrolyzed to the diacid or salt of the diacid defined by structure (6). For example, an appropriately substituted ketone (5), such as dimethyl 1,1-difluoro-2-oxo-4,8,12-trimethyl-3,7,11-tridecatrienylphosphonate is combined with approximately 2 equivalents of collidine in a suitable organic solvent, such as dichloromethane, and cooled to approximately 0° C. Approximately 3 to 4 equivalents of a suitable trialkylsilyl halide, such as trimethylsilyl bromide, is added dropwise to the above solution. The reaction is then allowed to warm to ambient temperature. After stirring for about 5 hours, the reaction is diluted with a suitable organic solvent, such as toluene. The solvent is removed under vacuum and the residue is dissolved in a suitable organic solvent, such as diethyl ether, and rinsed with a suitable aqueous acid, such as 1N hydrochloric acid. This is treated with an excess of a suitable base, such as 0.1N sodium hydroxide, concentrated under vacuum to remove the organic solvents and then lyophillized to remove the water. The product is then purified by techniques well known in the art. For example, the product can be purified by chromatography on a suitable stationary phase, such as CHP20P (a divinylbenzene/styrene copolymer) with an suitable eluent, such as a gradient from water to methanol to provide the disodium salt of 1,1-difluoro-2-oxo-4,8,12-trimethyl-3,7,11-tridecatrienyl-phosphonic acid.

The compounds of Formula II can be prepared as described in Scheme II. All the substituents unless otherwise indicated are previously defined. The reagents and starting materials are readily available to one of ordinary skill in the art.

Scheme II

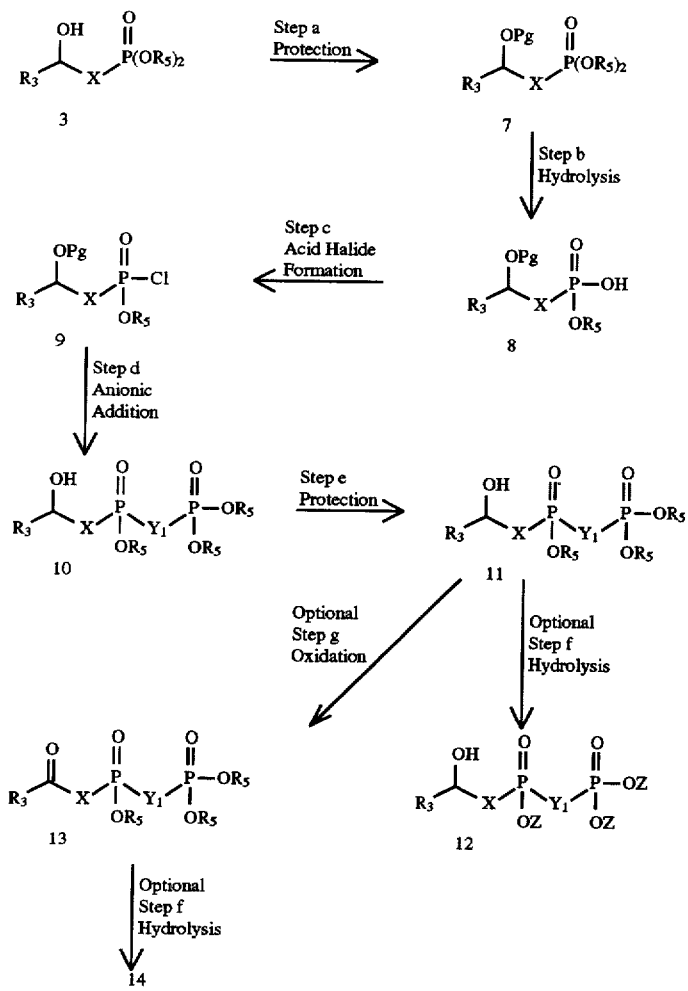

$R_5 = R_1$, $R_2$ and $R_3$, with the proviso that $R_5$ is not hydrogen or a pharmaceutically acceptable cation.
$Z$ = hydrogen or a pharmaceutically acceptable cation
$Y_1 = CH_2$ or $CF_2$ In scheme II, step a, the alcohol (3) is protected with a suitable protecting group, such as the t-butyldiphenylsilyl ether or the t-butyldimethylsilyl ether, the most preferred being the t-butyldiphenylsilyl ether, to provide the appropriately substituted protected alcohol described by structure (7).

For example, following generally the procedure described by Hanessian, S. and Lavellee, P., *J. Can. Chem.* 1975, 53, 2975, the alcohol (3) is dissolved in a suitable solvent such as dimethylformamide and treated with approximately 1.1 equivalents of t-butyldiphenylsilyl chloride and approximately 2.2 equivalents of imidazole. The reaction is stirred at room temperature for 4 to 24 hours. The reaction is then diluted with diethyl ether, rinsed with water, saturated sodium chloride diluted by half with water, saturated sodium chloride, dried over a suitable drying agent, such as anhydrous sodium sulfate, filtered and concentrated under vacuum. The residue is purified by techniques well known to one skilled in the art. For example the residue can be purified by flash chromatography with a suitable eluent, such as ethyl acetate/hexane, to provide the protected alcohol described by structure (7).

In scheme II, step b the protected alcohol (7) is selectively hydrolyzed to provide the appropriately substituted monoacid described by structure (8).

For example, following generally the procedure described by Biller, S. A. and Forster, C. *Tetrahedron* 1990, 46(19) 6645, the protected alcohol (7) is dissolved in a suitable solvent mixture, such as 1:1 methanol/water containing a slight excess of potassium hydroxide. The reaction is heated to 65°–75° C. for 1 to 5 hours. The methanol is then evaporated and methylene chloride is added. The stirring mixture is acidified with potassium hydrogen sulfate. The layers are separated and the aqueous layer is extracted with methylene chloride. The organic extracts are combined, washed with 50% brine, dried over anhydrous magnesium sulfate, filtered and concentrated to provide the monoacid (8).

In scheme II, step c, the monoacid (8) is treated with oxalyl chloride to form the appropriately substituted acid chloride described by structure (9).

For example, the monoacid (8) is dissolved in a suitable organic solvent, such as benzene, containing a catalytic amount of dimethylformamide under an atmosphere of nitrogen. An excess of oxalyl chloride is added dropwise at room temperature. After 2 to 4 hours the solution is concentrated under vacuum. The residue is then twice dissolved in benzene and concentrated under vacuum to provide the acid chloride (9).

In scheme II, step d, the acid chloride (9) is treated with a suitable anion to provide the appropriately substituted phosphonate described by structure (10).

For example, a solution of approximately 2.2 equivalents of an appropriately substituted dialkylphosphonate, such as dimethyl methylphosphonate, in a suitable organic solvent, such as tetrahydrofuran, is cooled to approximately −78° C. and treated dropwise with approximately 2.1 equivalents of butyllithium (1.6M in hexane). After stirring for approximately 15 to 30 minutes, an equivalent of the acid chloride (9) dissolved in tetrahydrofuran is added dropwise to the above formed anion. After stirring at −78° C. for approximately 1 hour, the reaction is allowed to warm to 0° C. and stir for an additional hour. Then the reaction is diluted with a suitable organic solvent, such as diethyl ether, and is quenched with a suitable aqueous acid, such as 10% hydrochloric acid. The phases are separated and the organic phase is rinsed with water, saturated sodium bicarbonate and brine. The mixture is dried over anhydrous magnesium sulfate, filtered and concentrated under vacuum. The residue is purified using techniques well known to one skilled in the art. For example, the residue can be purified by flash chromatography on silica gel using a suitable eluent, such as methanol/methylene chloride, to provide the purified phosphonate (10).

In scheme II, step e, the phosphonate (10) is deprotected under mild conditions to provide the alcohol described by structure (11).

For example, a solution of the phosphonate (10) is dissolved in a suitable organic solvent, such as tetrahydrofuran, and treated with an excess of a suitable fluoride ion source, such as tetra-n-butyl-ammonium fluoride, at ambient temperature. After approximately 1–24 hours the reaction is diluted with a suitable organic solvent, such as diethyl ether. The reaction is then rinsed with water, brine, dried over anhydrous magnesium sulfate, filtered and concentrated under vacuum. The residue is purified by techniques well known to one skilled in the art. For example, the residue can be purified by flash chromatography on silica gel using a suitable eluent, such as methanol/methylene chloride, to provide the purified alcohol (11).

In scheme II, step f the alcohol (11) can be hydrolyzed following generally the procedure previously described in scheme I, step c to provide the compound described by structure (12).

In scheme II, step g the alcohol (11) can be oxidized following generally the procedure previously described in scheme I, step b to provide the ketone described by structure (13).

In scheme II, step f the ketone (13) can be hydrolyzed following generally the procedure previously described in scheme I, step c to provide compound (14) in which R$_5$=Z.

The following examples present typical syntheses as described by Schemes I and II. These examples are understood to be illustrative only and are not intended to limit the scope of the invention in any way. As used in the following examples, the following terms have the meanings indicated: "eq." refers to equivalents, "g" refers to grams, "mg" refers to milligrams, "mmol" refers to millimoles, "mL" refers to milliliters, "°C." refers to degrees Celsius, "TLC" refers to thin layer chromatography, "R$_f$" refers to retention factor and "LOD" refers to lose on drying.

Example 1

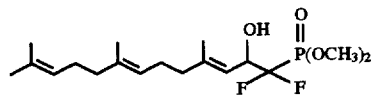

Preparation of dimethyl 1,1-difluoro-2-hydroxy-4,8,12-trimethyl-3,7,11-tridecatrienylphosphonate.

Scheme I, step a; Combine diisopropylamine (22.24 mL, 0.159 mol) with tetrahydrofuran (250 mL) and cool to −20° C. Add n-butyllithium (63.3 mL, 2.5N in hexane, 0.159 mol) dropwise to the solution. Stir for 30 minutes and cool to −78° C. Add dropwise a solution of dimethyl difluoromethylphosphonate (25.8 g, 0.159 mol) in tetrahydrofuran (20 mL) while maintaining the temperature below −75° C. After addition is complete, stir for 2 minutes and then slowly add a solution of trans, trans-farnesal [prepared according to Biller, S. A; Forster, C. Tetrahedron 1990, 46(19), 6645](14 g, 0.0636 mol) prepared in step a above, in tetrahydrofuran (10 mL) maintaining the temperature below −72° C. After addition is complete, stir for an additional 2 hours at −78° C. and then pour the reaction into 0.1N hydrochloric acid (500 mL). Extract the reaction with diethyl ether (2×1L). Combine the organic phases, dry over anhydrous magnesium sulfate, filter and concentrate under vacuum. Purify the residue by flash chromatography [40% ethyl acetate/hexane, R$_f$(50% ethyl acetate/hexane)=0.44] to provide the title compound (9.3 g, 39%) as an oil.

Anal. Calcd for C$_{18}$H$_{31}$F$_2$O$_4$P: C, 56.83; H, 8.21.
Found: C, 56.61; H, 8.48.

Example 2

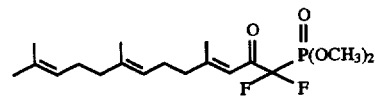

Preparation of dimethyl 1,1-difluoro-2-oxo-4,8,12-trimethyl-3,7,11-tridecatrienylphosphonate.

Scheme I, step b; Combine trifluoroacetic acid anhydride (1.30 mL, 0.0096 mol) with dichloromethane (20 mL) and cool to −60° C. Add dropwise a solution of dimethylsulfoxide (1.30 mL, 0.0183 mol) in dichloromethane (2 mL) while maintaining the temperature below −55° C. After addition is complete, stir for stir for 2 minutes. Add a solution of the dimethyl 1,1-difluoro-2-hydroxy-4,8,12-trimethyl-3,7,11-tridecatrienylphosphonate (1.60 g, 0.0042 mol) prepared in example 1 in dichloromethane (4 mL) and stir for 45 minutes. Cool the reaction to −78° C. and add triethylamine (3.0 mL, 0.021 mol) dropwise. Allow the reaction to warm to ambient temperature and stir for 45 minutes. Pour the reaction into water (100 mL). Extract this mixture with diethyl ether (400 mL). Dry the organic phase over anhydrous magnesium sulfate, filter and concentrate under vacuum. Purify the residue by flash chromatography (20% ethyl acetate/hexane, R$_f$=0.18) to provide the title compound (1.1 g, 69%) as an oil.

Anal. Calcd for C$_{18}$H$_{29}$F$_2$O$_4$P: C, 57.13; H, 7.72.
Found: C, 57.10; H, 7.97.

Example 3

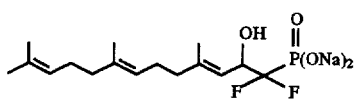

Preparation of 1,1-difluoro-2-hydroxy-4,8,12-trimethyl-3,7,11-tridecatrienylphosphonate, disodium salt.

Scheme I, step c; Combine dimethyl 1,1-difluoro-2-hydroxy-4,8,12-trimethyl-3,7,11-tridecatrienylphosphonate (0.378 g, 0.001 mol) prepared in example 1 with collidine (0.44 mL, 0.0033 mol) and dichloromethane (5 mL). Cool to 0° C. Add dropwise a solution of trimethylsilyl iodide (0.56 mL, 0.004 mol) in dichloromethane (0.5 mL) and allow the reaction to stir for 2 hours. Add diethyl ether (200 mL) and wash with 1N hydrochloric acid (3×100 mL). Dry the organic phase over anhydrous sodium sulfate, filter and concentrate under vacuum to provide the phosphonic acid of the title compound. Treat the residue with 0.1N sodium hydroxide (25 mL) and lyophillize to produce an off-white powder. Purify by chromatography on CHP20P (a divinylbenzene/styrene copolymer) eluting with a gradient, starting with water and finishing with methanol. Lyophillize the product containing fractions to provide the title compound (0.17 g, 43%) as a white powder, mp 287°–289° C.

Anal. Calcd for $C_{16}H_{25}F_2O_4PNa_2$: C, 48.48; H, 6.36.
Found: C, 48.20; H, 6.32.

Example 4

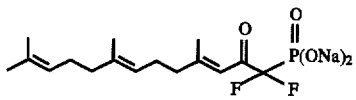

Preparation of 1,1-difluoro-2-oxo-4,8,12-trimethyl-3,7,11-tridecatrienylphosphonate, disodium salt.

Scheme I, step d; Combine dimethyl 1,1-difluoro-2-oxo-4,8,12-trimethyl-3,7,11-tridecatrienylphosphonate (1.2 g, 0.0032 mol), prepared in example 2 with collidine (0.85 mL, 0.0064 mol) and dichloromethane (5 mL). Cool to 0° C. Add trimethylsilyl bromide (0.92 mL, 0.007 mol), warm to ambient temperature and stir for 5 hours. Add toluene (20 mL) and concentrate under vacuum. Add diethyl ether (200 mL) and wash with 1N hydrochloric acid (3×50 mL). Treat the organic phase with 0.1N sodium hydroxide (64 mL), concentrate under vacuum to remove the organic solvents and lyophillize to remove the water. Purify by chromatography as in example 3 and lyophillize the product containing fractions to provide the title compound (0.32 g, 25%) as a white powder, mp 247.5°–249° C. (dec.).

Anal. Calcd for $C_{16}H_{23}F_2O_4PNa_2 \cdot 0.8H_2O$: C, 47.02; H, 6.09, LOD=3.7.
Found: C, 47.05; H, 6.07, LOD=3.7.

Example 5

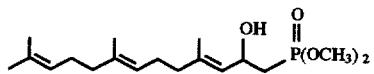

Preparation of dimethyl 2-hydroxy-4,8,12-trimethyl-3,7,11-tridecatrienyl phosphonate.

Scheme I, step a; Combine diisopropylamine (2.80 mL, 0.02 mol) with tetrahydrofuran (40 mL) and cool to –20° C. Add n-butyllithium (8.0 mL, 2.5N in hexane, 0.02 mol) dropwise to the solution. Stir for 20 minutes and cool to –70° C. Add dropwise a solution of dimethyl methylphosphonate (2.48 g, 0.020 mol) in tetrahydrofuran (20 mL) while maintaining the temperature below –70° C. After addition is complete, stir for 1 hour and then slowly add a solution of trans, trans-farnesaldehyde [prepared as in example 1] (2.2 g, 0.01 mol) in tetrahydrofuran (4 mL) maintaining the temperature below –72° C. After addition is complete, stir for an additional 1 hour at –70° C. and then pour the reaction into saturated ammonium chloride (100 mL). Extract the reaction with diethyl ether (400 mL). Dry the organic phase over anhydrous magnesium sulfate, filter and concentrate under vacuum. Purify the residue by flash chromatography (50% ethyl acetate/hexane, $R_f$=0.083) to provide the title compound (1.97 g, 57%) as an oil; MS (EI) M$^+$=344.

Anal. Calcd for $C_{18}H_{33}O_4P$: C, 62.77; H, 9.66.
Found: C, 62.75; H, 9.74.

Example 6

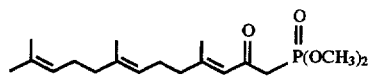

Preparation of dimethyl 2-oxo-4,8,12-trimethyl-3,7,11-tridecatrienyl phosphonate.

Scheme I, step b; Combine dimethyl 2-hydroxy-4,8,12-trimethyl-3,7,11-tridecatrienyl phosphonate (1.03 g, 0.003 mol) prepared in example 5 with barium permanganate (2.30 g, 0.009 mol) and dichloromethane (18 mL) under a nitrogen atmosphere. Stir for 6 days. Remove the solids by filtration and concentrate the filtrate under vacuum. Purify the residue by flash chromatography (75% ethyl acetate/hexane, $R_f$=0.51) to provide the title compound (0.3 g, 30%) as an oil; MS (CI/CH$_4$) M+H=343.

Anal. Calcd for $C_{18}H_{31}O_4P$: C, 63.13; H, 9.13.
Found: C, 61.96; H, 9.22.

Example 7

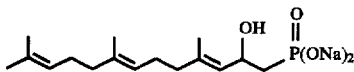

Preparation of 2-hydroxy-4,8,12-trimethyl-3,7,11-tridecatrienyl phosphonate, disodium salt.

Scheme I, step c; Combine dimethyl 2-hydroxy-4,8,12-trimethyl-3,7,11-tridecatrienyl phosphonate (0.95 g, 0.0027 mol) with collidine (0.73 mL, 0.0055 mol) and dichloromethane (7.5 mL). Cool to 0° C. Add trimethylsilyl bromide (1.44 mL, 0.011 mol) and warm to ambient temperature. Stir for 5 hours and add toluene (20 mL). Concentrate under vacuum and dissolve the residue in diethyl ether (200 mL). Rinse with 1N hydrochloric acid (3×50 mL). Add 0.1N sodium hydroxide (54 mL) to the organic phase, remove the organic solvents under vacuum and lyophillize to remove the water. Purify by chromatography as in example 3 to provide the title compound (0.35 g, 35%) as a white lyophillate, mp>350° C.

Anal. Calcd for $C_{16}H_{27}O_4PNa_2 \cdot 0.6H_2O$: C, 51.78; H, 7.66, LOD 2.9.
Found: C, 51.48; H, 7.66, LOD 2.9.

Example 8

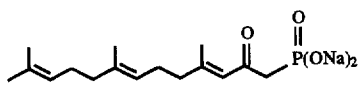

Preparation of 2-oxo-4,8,12-trimethyl-3,7,11-tridecatrienyl phosphonate, disodium salt.

Scheme I, step c; Combine dimethyl 2-oxo-4,8,12-trimethyl-3,7,11-tridecatrienyl phosphonate (0.692 g, 0.002 mol) with collidine (0.53 mL, 0.004 mol) and dichloromethane (5 mL). Cool to 0° C. Add trimethylsilyl bromide (1.05 mL, 0.008 mol) and warm to ambient temperature. Stir for 4 hours and then concentrate under vacuum. Dissolve the residue in diethyl ether (100 mL) and rinse with 1N hydrochloric acid (3×50 mL). Add 0.1N sodium hydroxide (40 mL) to the organic phase, remove the organic solvents under vacuum and lyophillize to remove the water to provide a white powder. Purify by chromatography as described in example 3 to provide the title compound (0.34 g, 44%) as a white powder, mp >360° C.

Anal. Calcd for $C_{16}H_{25}O_4PNa_2 \cdot 1.15H_2O$: C, 50.69; H, 7.26, LOD 5.5.

Found: C, 50.54; H, 7.53, LOD 5.5.

Example 9

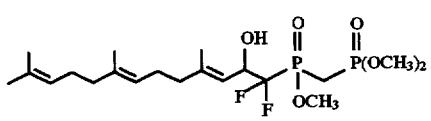

Preparation of methyl [(1,1-difluoro-2-hydroxy-4,8,12-trimethyl-3,7,11-tridecatrienyt)methyl phosphonic acid, dimethyl ester]phosphinate.

Scheme II, step a; Dissolve dimethyl 1,1-difluoro-2-hydroxy-4,8,12-trimethyl-3,7,11-tridecatrienylphosphonate (1.0 eq.) prepared in example 1, in tetrahydrofuran. Treat with t-butyldiphenylsilyl chloride (1.1 eq.) and imidazole (2.2 eq.) at room temperature with stirring. After 8 hours dilute the reaction with ether and rinse with water, brine, dry over anhydrous magnesium sulfate, filter and concentrate under vacuum. Purify the residue by flash chromatography on silica gel (ethyl acetate/hexane) to provide the protected alcohol.

Scheme II, step b; Dissolve the above formed protected alcohol (1.0 eq.) in methanol/water, 1:1, containing potassium hydroxide (1.1 eq.) and heat the reaction to 65° C. for 1 hour. Evaporate the methanol and add an equivalent amount of methylene chloride. With stirring acidify the mixture with potassium hydrogen sulfate. Separate the layers and extract the aqueous layer with methylene chloride. Combine the organic extracts, wash with 50% brine, dry over anhydrous magnesium sulfate, filter and concentrate under vacuum to provide the monoacid.

Scheme II, step c; Dissolve the above formed monoacid (1.0 eq.) in dry benzene under nitrogen and add a catalytic amount of dimethylformamide. Treat the solution with oxalyl chloride (3.0 eq.) dropwise at room temperature and stir for 4 hours. Concentrate the reaction under vacuum, add an equivalent amount of benzene as above, concentrate under vacuum and repeat this process one more time to provide the acid chloride.

Scheme II, step d; Dissolve dimethyl methylphosphonate (2.2 eq.) in dry tetrahydrofuran and cool to −78° C. Add dropwise to the solution butyllithium (2.1 eq. of a 1.6M solution in hexane). After addition is complete, stir the reaction for 30 minutes. Dissolve the above formed acid chloride (1.0 eq.) in dry tetrahydrofuran and add dropwise to the anion. After addition is complete, stir the reaction for 1 hour at −78° C., warm to 0° C. and stir for an additional hour. Dilute the reaction with diethyl ether and quench the reaction with 10% hydrochloric acid. Separate the phases and wash the organic phase with water, saturated sodium bicarbonate, brine, dry over anhydrous magnesium sulfate, filter and concentrate under vacuum. Purify the residue by flash chromatography on silica gel (methanol/methylene chloride) to provide the methyl phosphinate dimethyl phosphonate.

Scheme II, step e; Dissolve the above formed methyl phosphinate dimethyl phosphonate (1.0 eq.) in tetrahydrofuran and add tetrabutylammonium fluoride (2.0 eq. of a 1M solution in tetrahydrofuran). Stir the reaction at room temperature for 20 hours and dilute with diethyl ether. Rinse the organic with water, brine, dry over anhydrous magnesium sulfate, filter and concentrate under vacuum. Purify the residue by flash chromatography on silica gel (methanol/methylene chloride) to provide the title compound.

Example 10

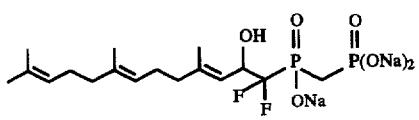

Preparation of [(1,1-difluoro-2-hydroxy-4,8,12-trimethyl-3,7,11-tridecatrienyl)methyl phosphonate, disodium salt] phosphinate, sodium salt.

Scheme II, step f; Combine the methyl phosphinate dimethyl phosphonate (1 eq.) prepared in example 9 with collidine (3.3 eq.) and dichloromethane. Cool to 0° C. and add dropwise a solution of trimethylsilyl iodide (4 eq.) in dichloromethane. Allow the reaction to stir for 2 hours. Add diethyl ether and wash with 1N hydrochloric acid. Dry the organic phase over anhydrous sodium sulfate, filter and concentrate under vacuum to provide the triacid of the title compound. Treat the residue with excess 0.1N sodium hydroxide and lyophillize. Purify by chromatography on CHP20P (a divinylbenzene/styrene copolymer) eluting with a gradient, starting with water and finishing with methanol. Lyophillize the product containing fractions to provide the title compound.

Example 11

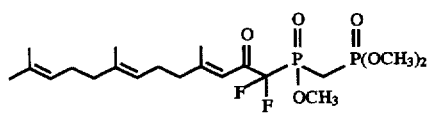

Preparation of methyl[(1,1-difluoro-2-oxo-4,8,12-trimethyl-3,7,11-tridecatrienyl)methyl phosphonate, dimethyl ester] phosphinate.

Scheme II, step g; Combine trifluoroacetic acid anhydride (1.0 eq.) with dichloromethane and cool to −60° C. Add dropwise a solution of dimethylsulfoxide (2.0 eq) in dichloromethane while maintaining the temperature below −55° C. After addition is complete, stir for 2 minutes. Add a solution of the methyl phosphinate dimethyl phosphonate (1 eq) prepared in example 9 in dichloromethane and stir for 45 minutes. Cool the reaction to −78° C. and add triethylamine (3 eq.) dropwise. Allow the reaction to warm to ambient temperature and stir for 45 minutes. Pour the reaction into

Example 12

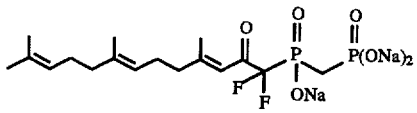

Preparation of [(1,1-difluoro-2-oxo-4,8,12-trimethyl-3,7,11-tridecatrienyl)methyl phosphonater disodium salt] phosphinater sodium salt.

Scheme II, step f; Combine the methyl phosphinate dimethyl phosphonate (1.0 eq.), prepared in example 11 with collidine (2.0 eq.) and dichloromethane. Cool to 0° C. and add trimethylsilyl bromide (2.1 eq.). Warm to ambient temperature and stir for 5 hours. Add toluene and concentrate under vacuum. Add diethyl ether and wash with 1N hydrochloric acid. Treat the organic phase with excess 0.1N sodium hydroxide, concentrate under vacuum to remove the organic solvents and lyophillize to remove the water. Purify by chromatography as in example 10 and lyophillize the product containing fractions to provide the title compound.

Example 13

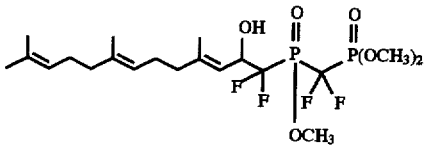

Preparation of methyl [(1,1-difluoro-2-hydroxy-4,8,12-trimethyl-3,7,11-tridecatrienyl)difluoromethyl phosphonic acid, dimethyl ester]phosphinate.

Scheme II, step d; Add dimethyl difluoromethylphosphonate in dry tetrahydrofuran to a solution of lithium diisopropylamide (1.05 eq) at −78° C. After addition is complete, stir the reaction for 30 minutes. Dissolve the acid chloride (1.0 eq.) [formed in example 9, steps a through c] in dry tetrahydrofuran and add dropwise to the anion. After addition is complete, stir the reaction for 1 hour at −78° C., warm to 0° C. and stir for an additional hour. Dilute the reaction with diethyl ether and quench the reaction with 10% hydrochloric acid. Separate the phases and wash the organic phase with water, saturated sodium bicarbonate, brine, dry over anhydrous magnesium sulfate, filter and concentrate under vacuum. Purify the residue by flash chromatography on silica gel (methanol/methylene chloride) to provide the difluoromethyl phosphinate dimethyl phosphonate.

Scheme II, step e; Dissolve the above formed difluoromethyl phosphinate dimethyl phosphonate (1.0 eq.) in tetrahydrofuran and add tetrabutylammonium fluoride (2.0 eq. of a 1M solution in tetrahydrofuran). Stir the reaction at room temperature for 20 hours and dilute with diethyl ether. Rinse the organic with water, brine, dry over anhydrous magnesium sulfate, filter and concentrate under vacuum. Purify the residue by flash chromatography on silica gel (methanol/methylene chloride) to provide the title compound.

Example 14

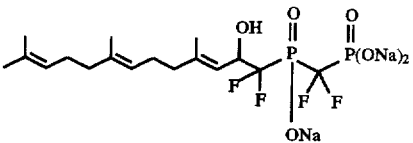

Preparation of [(1,1-difluoro-2-hydroxy-4,8,12-trimethyl-3,7,11-tridecatrienyl)difluoromethyl phosphonic acid, disodium salt]phosphinic acid, sodium salt.

Scheme II, step f; Combine the difluoromethyl phosphinate dimethyl phosphonate (1 eq.) prepared in example 17 with collidine (4.0 eq.) and dichloromethane. Cool to 0° C. and add dropwise a solution of trimethylsilyl bromide (5 eq.). Allow the reaction to stir for 5 hours. At room temperature add diethyl ether and wash with 1N hydrochloric acid. Dry the organic phase over anhydrous sodium sulfate, filter and concentrate under vacuum to provide the triacid of the title compound. Treat the residue with excess 0.1N sodium hydroxide and lyophillize. Purify by chromatography on CHP20P (a divinylbenzene/styrene copolymer) eluting with a gradient, starting with water and finishing with methanol. Lyophillize the product containing fractions to provide the title compound.

Example 15

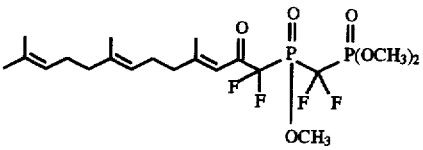

Preparation of methyl[(1,1-difluoro-2-oxo-4,8,12-trimethyl-3,7,11-tridecatrienyl)difluoromethyl phosphonate, dimethyl ester]phosphinate.

Scheme II, step g; Combine trifluoroacetic acid anhydride (1.0 eq.) with dichloromethane and cool to −60° C. Add dropwise a solution of dimethylsulfoxide (2.0 eq) in dichloromethane while maintaining the temperature below −55° C. After addition is complete, stir for 2 minutes. Add a solution of the difluoromethyl phosphinate dimethyl phosphonate (1 eq) prepared in example 17 in dichloromethane and stir for 45 minutes. Cool the reaction to −78° C. and add triethylamine (3 eq.) dropwise. Allow the reaction to warm to ambient temperature and stir for 45 minutes. Pour the reaction into water. Extract this mixture with diethyl ether. Dry the organic phase over anhydrous magnesium sulfate, filter and concentrate under vacuum. Purify the residue by flash chromatography (ethyl acetate/hexane) to provide the title compound.

Example 16

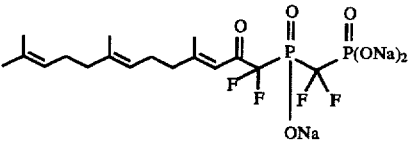

Preparation of [(1,1-difluoro-2-oxo-4,8,12-trimethyl-3,7,11-tridecatrienyl)difluoromethyl phosphonic acid, disodium salt]phosphinic acid, sodium salt.

Scheme II, step f; Combine the difluoromethyl phosphinate dimethyl phosphonate (1.0 eq.), prepared in example 19 with collidine (2.0 eq.) and dichloromethane. Cool to 0° C. and add trimethylsilyl bromide (2.1 eq.). Warm to ambient temperature and stir for 5 hours. Add toluene and concentrate under vacuum. Add diethyl ether and wash with 1N hydrochloric acid. Treat the organic phase with excess 0.1N sodium hydroxide, concentrate under vacuum to remove the organic solvents and lyophillize to remove the water. Purify by chromatography as in example 10 and lyophillize the product containing fractions to provide the title compound.

In a further embodiment, the present invention provides a method for the treatment of a patient afflicted with a neoplastic disease state comprising the administration thereto of a therapeutically effective antineoplastic amount of a compound of Formula I or II. The term "neoplastic disease state" as used herein refers to an abnormal state or condition characterized by rapidly proliferating cell growth or neoplasm. Neoplastic disease states for which treatment with a compound of Formula I or II will be particularly useful include: Leukemias such as, but not limited to, acute lymphoblastic, chronic lymphocytic, acute myloblastic and chronic mylocytic; Carcinomas, such as, but not limited to, those of the cervix, esophagus, stomach, small intestines, pancreas, colon and lungs; Sarcomas, such as, but not limited to, oesteroma, osteosarcoma, lepoma, liposarcoma, hemangioma and hemangiosarcoma; Melanomas, including amelanotic and melanotic; and mixed types of neoplasias such as, but not limited to carcinosarcoma, lymphoid tissue type, folicullar reticulum, cell sarcoma and Hodgkins Disease.

As used herein, the term "patient" refers to a warm-blooded animal, such as a human, which is afflicted with a particular neoplastic disease state.

A therapeutically effective antineoplastic amount of a compound of Formula I or II refers to an amount which is effective, upon single or multiple dose administration to the patient, in controlling the growth of the neoplasm or in prolonging the survivability of the patient beyond that expected in the absence of such treatment. As used herein, "controlling the growth" of the neoplasm refers to slowing, interrupting, arresting or stopping its growth and metastases and does not necessarily indicate a total elimination of the neoplasm.

As used herein, the term "therapeutically effective amount" refers to a therapeutically effective antineoplastic amount of a compound of the Formula I or II. A therapeutically effective amount can be readily determined by the attending diagnostician, as one skilled in the art, by the use of known techniques and by observing results obtained under analogous circumstances. In determining the therapeutically effective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

A therapeutically effective amount of a compound of Formula I or II is expected to vary from about 0.1 milligram per kilogram of body weight per day (mg/kg/day) to about 100 mg/kg/day. Preferred amounts are expected to vary from about 0.5 to about 25 mg/kg/day.

In effecting treatment of a patient afflicted with a disease state described above, a compound of Formula I or II can be administered in any form or mode which makes the compound bioavailable in effective amounts, including oral and parenteral routes. For example, compounds of Formula I or II can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected, the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

In another embodiment, the present invention provides compositions comprising a compound of Formula I or II in admixture or otherwise in association with one or more inert carriers. These compositions are useful, for example, as assay standards, as convenient means of making bulk shipments, or as pharmaceutical compositions. An assayable amount of a compound of Formula I or II is an amount which is readily measurable by standard assay procedures and techniques as are well known and appreciated by those skilled in the art. Assayable amounts of a compound of Formula I or II will generally vary from about 0.001% to about 75% of the composition by weight. Inert carriers can be any material which does not degrade or otherwise covalently react with a compound of Formula I or II. Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising a therapeutically effective amount of a compound of Formula I or II in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possesses a particular generic utility, certain groups and configurations are preferred for compounds of Formula I or II in their end-use application.

With respect to the substituent X, compounds of Formula I or II wherein X is $CF_2$ are generally preferred. With respect to the substituents $R_1$ and $R_2$, compounds of Formula I or II wherein $R_1$ and $R_2$ are Na are generally preferred. With respect to the substituent A, compounds of Formula I or II wherein A is 1-oxo-farnesyl are generally preferred.

The following list identifies compounds of the Formula I or II which are particularly preferred embodiments of the present invention:

Dimethyl 1,1-difluoro-2-hydroxy-4,8,12-trimethyl-3,7,11-tridecatrienylphosphonate;

Dimethyl 1,1-difluoro-2-oxo-4,8,12-trimethyl-3,7,11-tridecatrienylphosphonate;

1,1-Difluoro-2-hydroxy-4,8,12-trimethyl-3,7,11-tridecatrienylphosphonate, disodium salt;

1,1-Difluoro-2-oxo-4,8,12-trimethyl-3,7,11-tridecatrienylphosphonate, disodium salt;

Dimethyl 2-hydroxy-4,8,12-trimethyl-3,7,11-tridecatrienyl phosphonate;

Dimethyl 2-oxo-4,8,12-trimethyl-3,7,11-tridecatrienyl phosphonate;

2-Hydroxy-4,8,12-trimethyl-3,7,11-tridecatrienyl phosphonate, disodium salt;

2-Oxo-4,8,12-trimethyl-3,7,11-tridecatrienyl phosphonate, disodium salt;

Methyl [(1,1-difluoro-2-oxo-4,8,12-trimethyl-3,7,11-tridecatrienyl)methyl phosphonic acid, dimethyl ester] phosphinate and the sodium salts of the corresponding acids;

Methyl [(1,1-difluoro-2-oxo-4,8,12-trimethyl-3,7,11-tridecatrienyl)difluoromethyl phosphonic acid, dimethyl ester]phosphinate and the sodium salts of the corresponding acids;

Methyl [(1,1-difluoro-2-hydroxy-4,8,12-trimethyl-3,7,11-tridecatrienyl)difluoromethyl phosphonic acid, dimethyl ester]phosphinate and the sodium salts of the corresponding acids;

Methyl [(1,1-difluoro-2-hydroxy-4,8,12-trimethyl-3,7,11-tridecatrienyl)methyl phosphonic acid, dimethyl ester] phosphinate and the sodium salts of the corresponding acids;

Methyl [(2-oxo-4,8,12-trimethyl-3,7,11-tridecatrienyl) methyl phosphonic acid, dimethyl ester]phosphinate and the sodium salts of the corresponding acids;

Methyl [(2-oxo-4,8,12-trimethyl-3,7,11-tridecatrienyl) difluoromethyl phosphonic acid, dimethyl ester]phosphinate and the sodium salts of the corresponding acids;

Methyl [(2-hydroxy-4,8,12-trimethyl-3,7,11-tridecatrienyl)difluoromethyl phosphonic acid, dimethyl ester]phosphinate and the sodium salts of the corresponding acids;

Methyl [(2-hydroxy-4,8,12-trimethyl-3,7,11-tridecatrienyl)methyl phosphonic acid, dimethyl ester] phosphinate and the sodium salts of the corresponding acids;

What is claimed is:

1. A method of treating a patient afflicted with a neoplastic disease state selected from the group consisting of leukemia, lung carcinoma, colon carcinoma, and pancreas carcinoma comprising the administration thereto of a therapeutically effective antineoplastic amount of a compound of the formula

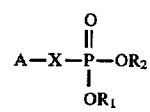

wherein X is $CCl_2$ or $CF_2$, $R_1$ and $R_2$ are each independently H; $C_1$-$C_4$ alkyl; $(CH_2)_n$-Z, wherein n is the integer 0,1,2,3 or 4 and Z is phenyl or naphthyl, unsubstituted or substituted with from 1 to 3 substituents selected from the group consisting of $C_1$-$C_4$ alkyl, $C_1$-$C_4$ alkoxy, halogen, $CF_3$, $OCF_3$, OH, CN, $NO_2$ and $NH_2$; or a pharmaceutically acceptable cation, and A is a radical selected from the group consisting of

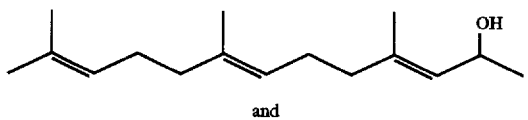

and

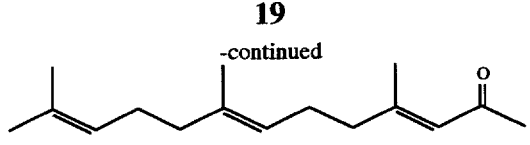

2. A method of controlling the growth of a neoplasm in a patient afflicted with a neoplastic disease state selected from the group consisting of leukemia, lung carcinoma, colon carcinoma, and pancreas carcinoma comprising administration thereto of a therapeutically effective antineoplastic amount of a compound of the formula

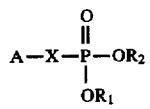

wherein X is $CCl_2$ or $CF_2$, $R_1$ and $R_2$ are each independently H; $C_1$-$C_4$ alkyl; $(CH_2)_n$-Z, wherein n is the integer 0,1,2,3 or 4 and Z is phenyl or naphthyl, unsubstituted or substituted with from 1 to 3 substituents selected from the group consisting of $C_1$-$C_4$ alkyl, $C_1$-$C_4$ alkoxy, halogen, $CF_3$, $OCF_3$, OH, CN, $NO_2$ and $NH_2$; or a pharmaceutically acceptable cation, and A is a radical selected from the group consisting of

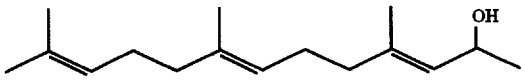

and

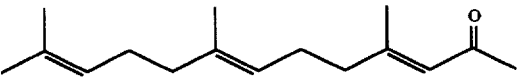

* * * * *

UNITED STATES PATENT AND TRADEMARK OFFICE
CERTIFICATE OF CORRECTION

PATENT NO. : 5,665,715

DATED : September 9, 1997

INVENTOR(s) : David M. Stemerick

It is certified that error appears in the above-identified patent and that said Letters Patent is hereby corrected as shown below:

At column 1, line 5, the patent reads "5,467,182" and should read --5,463,181--.
At column 2, line 5, in the structure, the patent reads "$RO_1$" and should read --$OR_1$--.
At column 2, line 36, the patent reads "refers an" and should read --refers to an--.
At column 2, line 37, the patent reads "an saturated" and should read --a saturated--.
At column 2, line 39, the patent reads "atoms included" and should read --atoms. Included-- .
At column 4, line 28, the patent reads "lyophitlized" and should read --lyophillized-- .
At column 4, line 32, and at line 58, the patent reads "an suitable" and should read --a suitable--.
At column 5, line 17, in the structure (10) the patent reads "OH" and should read --Opg--.
At column 5, line 17, Scheme II, the patent reads "Step e Protection" and should read --Step e Deprotection--.
At column 8, line 2, the patent reads "lose" and should read --loss--.
At column 8, line 52, the patent reads "stir for stir for 2 min." and should read --stir for 2 min.-- .
At column 11, line 34, the patent reads "tridecatrienyt)" and should read --tridecatrienyl)--.

Signed and Sealed this

Twenty-sixth Day of January, 1999

Attest:

Attesting Officer

*Acting Commissioner of Patents and Trademarks*